(12) United States Patent
Yang et al.

(10) Patent No.: US 6,495,708 B1
(45) Date of Patent: Dec. 17, 2002

(54) ALUMINOSILOXANE COMPOUND AND PROCESS FOR PREPARING THE SAME

(76) Inventors: Jae-Kun Yang, Joogong Apt. #606-1405, Gaepo-dong, Kangnam-ku, Seoul (KR); Jeong-Ryeon Han, Samwoo Villa #501, 48-30, Jangchoong-dong 1-ga, Joong-ku, Seoul (KR)

( * ) Notice: Subject to any disclaimer, the term of this patent is extended or adjusted under 35 U.S.C. 154(b) by 0 days.

(21) Appl. No.: 09/762,947
(22) PCT Filed: May 20, 2000
(86) PCT No.: PCT/KR00/00506
§ 371 (c)(1), (2), (4) Date: Feb. 14, 2001
(87) PCT Pub. No.: WO00/71553
PCT Pub. Date: Nov. 30, 2000

(30) Foreign Application Priority Data

May 21, 1999 (KR) ............................................ 99-18491

(51) Int. Cl.$^7$ ................................ C07F 5/06; C07F 7/21
(52) U.S. Cl. ........................ 556/10; 556/173; 252/182.3
(58) Field of Search ................. 556/10, 173; 252/182.3

(56) References Cited

U.S. PATENT DOCUMENTS

| | | | |
|---|---|---|---|
| 4,528,038 A | 7/1985 | Williams | 106/287.13 |
| 4,554,186 A | 11/1985 | Williams | 427/387 |
| 5,614,654 A | 3/1997 | Miyake et al. | 556/10 |

FOREIGN PATENT DOCUMENTS

JP     A10231366     9/1998

*Primary Examiner*—Porfirio Nazario-Gonzalez
(74) *Attorney, Agent, or Firm*—Birch, Stewart, Kolasch & Birch, LLP

(57) ABSTRACT

The present invention relates to novel aluminosiloxane compounds which have the characteristics to be prepared from waste silicone compounds and to be advantageously used as siloxylating agent for various organic and inorganic materials, processes for preparation thereof, and uses thereof.

16 Claims, 7 Drawing Sheets

ALUMINOSILOXANE COMPOUND AND PROCESS FOR PREPARING THE SAME

This application is the national phase under 35 U.S.C. §371 of PCT International Application No. PCT/KR00/00506 which has an International filing date of May 20, 2000, which designated the United States of America.

TECHNICAL FIELD

The present invention relates to novel aluminosiloxane compounds represented by the following formulae (1) and (2), processes for preparing same and use thereof. Particularly, the compounds of formulae (1) and (2) according to the present invention have the characteristics to be prepared from waste silicone compounds and to be advantageously used as siloxylating agent for various organic and inorganic materials, specifically for materials containing hydroxy group.

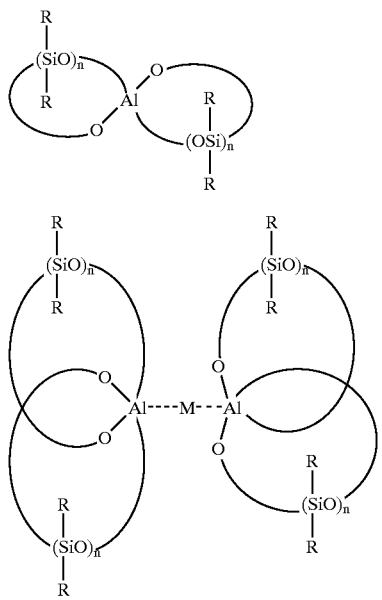

(1)

(2)

in which

R is identical with or different from each other, and represents $C_1$-$C_6$-alkyl or phenyl, n denotes a number of 6 to 90, and M represents alkali metal.

BACKGROUND ART

Currently used siloxylating agents include silane or siloxane compounds containing reactive hydroxy group(—OH), alkoxy group(—OR), carboxyl group (—OCOR), amine group(—NHR, —NR$_2$), epoxy group

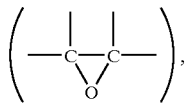

hydrogen(—H), etc at terminal sites of the molecules, and modified silyl compounds wherein silyl groups are bound to the intramolecular side chains.

The novel aluminosiloxane compounds provided by the present invention belong to hetero metallic siloxane series (≡Si—O—M—O—Si≡) wherein a metal atom is placed between two siloxane groups. The aluminosiloxane compounds according to the present invention not only can replace the existing siloxylating, agent, but also exhibit more strong siliconic characteristics through the formation of a long chain wherein at least six(6) dialkyl(or phenyl)siloxyl units

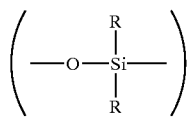

are linked with each other. Particularly, the present compounds are expected to have a highly improved properties in reactivity for siloxylation, etc.

Many researches have been made on aluminosiloxanes. For example, aluminosilsesquioxane prepared from isopropoxyaluminum[(i-PrO)$_2$Al] and trialkoxysilane is disclosed in J. Am. Chem. Soc. 1989, 111, 7288–7289 and Inorg Chem. 1999, 38, 210–211. This aluminosilsesquioxane compound is identical with the compounds of the present invention in that Al atom has a AlO$_4$ configuration, but different therefrom in that Si atom has a RSiO$_3$ configuration. Further, a method for endowing aluminum metal surface with anti-corrosion property and gloss by treating the metal surface with ethoxysilane vapour to form =Al—O—Si≡ bond on the metal surface(see: Journal of the Electrochemical Society V.143, N.1, 1996); a method for forming =Al—O—Si≡ structure on aluminum metal surface by treating the metal surface with alkoxysilane through a sol-gel method(see: Colloids and Surfaces A: Physicochem. Eng. Aspects 139, 299–310, 1998); a method for synthesizing phosphine ruthernium(Rh) complex by reacting isopropoxyaluminum with alkoxysilane through a sol-gel method(see: Inorg. Chem. 1997, 36, 862–866 and Chem. Mater. 1998, 10, 217–225); and a method for preparing mullite from aluminum and silicone oxide via aluminosiloxane(see: Chem. Mater, 1996, 8, 2056–2060) are disclosed. However, any of the intermediates or final products disclosed in these prior arts does not have a similar structure or property to the novel aluminosiloxane compound provided by the present invention.

Under the technical background as explained above, the present inventors have studied to develop an effective method for decomposition and recovery of siloxane bond-containing compound such as silicone rubber, silicone oil, etc., which ultimately results in decrease of pollution caused by waste silicone compounds and promotion of silicone chemical industry without any concern about waste. As a result, we filed an application for a novel process for decomposing siloxane bond-containing compound characterized in that secondary and/or tertiary aliphatic alcohols are used as a decomposition facilitator, and if desired, the decomposition product is further sonicated and treated with a terminator. The application has now been granted a patent (see, Korean Patent No 190,752, and U.S. Pat. No. 5,892, 087). Specifically, the siloxane bond has the advantage of excellent weatherability whereby it is not aged nor decomposed But, such an advantage rather causes the impossibility of natural decomposition after waste of the siloxane bond-containing compounds, which makes them serious pollutional materials. Therefore, the development of said decomposition or recovery process is considered to have a great importance in the aspect of environmental protection.

The present inventors proceeded with our studies to develop a compound which can be effectively utilized as a siloxylating agent by using a siloxane alkali metal salt represented by the following formula (3), which is obtained through the aforementioned decomposition process, as the starting material. Accordingly, the present inventors have synthesized the compounds of formulae (1) and (2) as above and identified structures and uses thereof, and then completed the present invention:

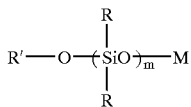

in which
R is identical with or different from each other, and represents $C_1$–$C_6$-alkyl or phenyl,
R' represents hydrogen or $C_1$–$C_6$-alkyl,
M represents alkali metal, and
m denotes a number of 3 to 6.

The present invention will be more specifically explained hereinafter.

DISCLOSURE OF INVENTION

One object of the present invention is to provide aluminosiloxane compounds of the following formula (1) or (2):

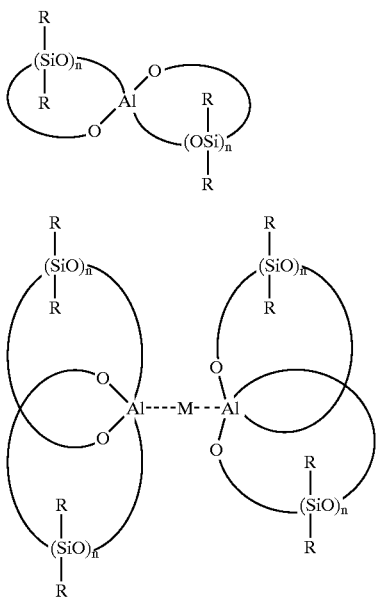

in which

R is identical with or different from each other, and represents $C_1$–$C_6$-alkyl or phenyl, n denotes a number of 6 to 90, and M represents alkali metal.

As can be seen from the above formulae (1) and (2), silicon atoms in the aluminosiloxane compound of the present invention are identified through $^{29}$Si-NMR to have the configuration of dialkyl(or phenyl)siloxyl unit

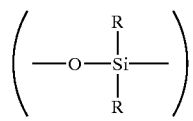

wherein two(2) oxygen atoms and two(2) alkyl(or phenyl) groups are attached to the silicon atom, and aluminum atoms are identified through $^{27}$Al-NMR to have the configuration coordinated with four(4) oxygen atoms.

The present compounds characterized by such an unique structure have different molecular weights depending on R, M and n. Further, with the content of M, the compound of formula (1) seems to be associated to form the compound of formula (2). That is, according to G.P.C. molecular weight measurement, the compound of formula (2) having an average molecular weight of 2000 wherein R is methyl, n is 6, and M is natrium(Sample 1 of the following Table 1) may be converted to the compound of formula (1) having an average molecular weight of 1000(Sample 2 of the following Table 1) by the treatment with ammonium chloride (purification=removal of natrium) during which the content of natrium is significantly decreased(1.51%→0.55%). Elementary analysis results and n values calculated therefrom for some typical compounds according to the present invention are represented in the following Table 1.

TABLE 1

| Sample No | C (%) | H (%) | O (%) | Si (%) | Al (%) | Na (%) | Molecular Weight Calculated | Molecular Weight Found by GPC | Si/Al | n value |
|---|---|---|---|---|---|---|---|---|---|---|
| 1 | 30.75 | 6.27 | 22.88 | 35.84 | 2.76 | 1.51 | 1963.70 | 2,000 | 12 | 6 |
| 2 | 30.82 | 6.28 | 22.89 | 35.8 | 2.85 | 0.55 | 903.27 | 1,000 | 12 | 6 |
| 3 | 31.59 | 6.59 | 23.9 | 36.82 | 0.52 | 0.3 | 5,250.60 | 5,462 | 70 | 35 |
| 4 | 32.41 | 7.67 | 23.21 | 36.68 | 0.3 | 0.2 | 10,042.70 | 10,948 | 130 | 65 |

As can be seen from the elementary analysis results of the above Table 1, it has been found that aluminum content is 0.52% and average molecular weight is 5,462(see FIG. 3) in the case of Sample 3(object compound of Example 5) and aluminum content is 0.3% and average molecular weight is 10,948 in the case of Sample 4(object compound of Example 6). If calculated from the elementary analysis results, the n value of Sample 3 is 35 and that of Sample 4 is 65, respectively. Samples 3 and 4 are prepared using different amount of powdered aluminum metal from each other(see Examples 5 and 6). Therefore, it is realized that if the amount of aluminum(starting material) is controlled in the process for preparing the aluminosiloxane compound of the present invention, the n value may be optionally controlled. Upon conducting elementary analyses on the compounds having various molecular weights including the analyses of Table 1, it is identified that 12 to 180 silicon atoms are present for each aluminum atom in the aluminosiloxane compounds of formulae (1) and (2) according to the present invention.

Generally, physico-chemical properties of the aluminosiloxane compound vary depending on the n value. For example, flexibility increases as the n value increases, but if the n value comes close to 90, the compound having such a high n value almost has the state of liquid, which makes the handling thereof difficult(for that reason, the n value is restricted to 90 or less in the present invention). Further, since there is a case requiring high silicone-based properties or a case requiring low silicone-based properties depending on the purpose, it is desirable to prepare an aluminosiloxane compound having a specific n value appropriate for the purpose thereof by considering the correlation between the n value and physico-chemical property.

The aluminosiloxane compounds according to the present invention are soluble in nonpolar organic solvents such as n-hexane, benzene, toluene, tetrahydrofuran, etc. They are stable compounds having, a specific density varying from 0.94 to 0.98, and also stable under atmosphere in the form of gel solid. But, they are not stable in the presence of electron acceptor(H=proton) to be easily dissociated as depicted in the following Reaction Scheme 1.

[Reaction Scheme 1]

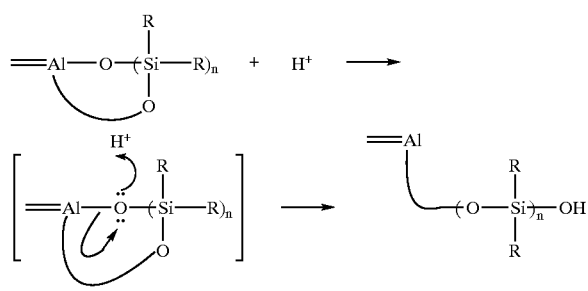

Therefore, according to the characteristics as described above, it is considered that condensation reaction may be actively carried out between organic or inorganic substance having hydroxy group or epoxy group at terminals, such as for example, thermosetting resin, cellulose, sucrose, epoxy, and the like and the product obtained from Reaction Scheme 1 optionally in the presence of an acid catalyst The condensation reaction is described in Reaction Scheme 2 below.

[Reaction Scheme 2]

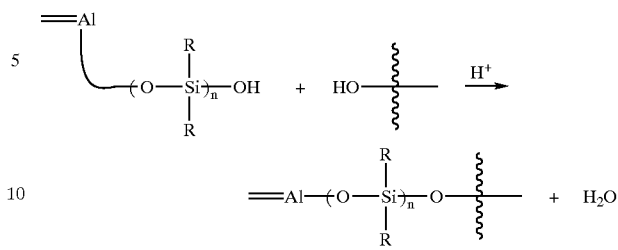

In the above Reaction Scheme 2, if the compound containing hydroxy group is a hydrocarbon compound and the resulting product has a structure of ≡Si—O—C≡, this linkage is unstable under atmosphere and thus, may have the problem to be readily dissociated again. However, inside the network structure of thermosetting resins such as phenol, melamine, urea, epoxy resins, or inside the macromolecules such as cellulose, the siloxane group may form a hybrid structure or stable interpenetrating polymer networks(IPN) which is caused by rearrangement from ≡Si—O—C≡ to siloxane(≡Si—O—Si≡) bond. Therefore, it is anticipated that compounds of the present invention may be used as a useful siloxylating agent for those thermosetting resins or macromolecules having a network structure. That is, if the aluminosiloxane compound according to the present invention is applied in the final step of preparing those thermosetting resins or macromolecules such as cellulose, the final product may be improved in its physico-chemical properties such as gloss, flexibility, water repellence, heat stability, weatherability, etc.

Further, the aluminosiloxane compound of the present invention may be effectively used as a siloxylating agent for the surface of glass products made from metallic silicate. This is because the aluminosiloxane compound is decomposed in the presence of an acid to have reactive functional groups such as

or

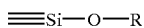

(wherein R is hydrogen or alkyl) at terminals, and the functional groups are readily reacted with HO—Si≡ group on the surface of glass products to form a strong bond.

Therefore, compound of formula (1) or (2) according to the present invention can be used as a superior siloxylating agent for the surface of thermosetting resins, cellulose, epoxy, metallic silicates, pigments made from various metallic oxides and other microorganisms to silanes having the existing functional groups. Therefore, another object of the present invention is to provide such a use. Particularly, when the compound of the present invention is used as a siloxylating agent, each siloxylation is carried out with minimum 6 to maximum 90 dialkyl(or phenyl)siloxyl units

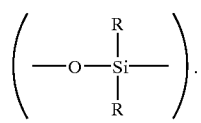

Therefore, materials siloxyated therewith show well established siloxane-based characteristics.

Siloxylation with the aluminosiloxane compounds of the present invention can be carried out in a conventional manner. However, in case of the materials which form a IPN structure during the siloxylation procedure, such as for example epoxy resins, the aluminosiloxane compound according to the present invention is mixed with the epoxy resin in the ratio of 9:1 to 5:5, preferably 8:2 to 7:3 by weight to form a copolymer first and then this copolymer is properly mixed with the epoxy resin to carry out siloxylation procedure.

The desirable amount when used as a siloxylating agent may be easily determined by the person skilled in the art considering the material to be siloxylated, specific structure of the siloxylating agent and the purpose of siloxylation. Generally, the siloxylating agent is used in an amount of 2 to 10% by weight, preferably 2 to 6% by weight with respect to the material to be siloxylated. When the siloxylating agent is not used in the amount as defined above, it may cause some deterioration of physico-chemical properties of the target material or insufficient siloxylation which does not come up to the expectation.

The aluminosiloxane compound of formula (2) according to the present invention can be prepared by a process characterized in that (i) the siloxane alkali metal salt of formula (3) is reacted with aluminum compound and secondary or tertiary alcohol to produce a hydrophilic compound represented by the following formula (4):

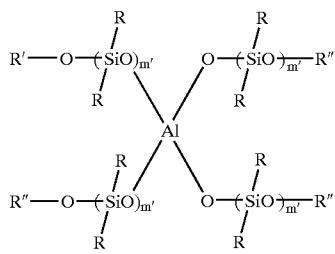

(4)

in which

R and R' are defined as previously described,

R'' is identical with or different from each other, and represents R' or M, but with at least one of R'' being different from R', and m' is identical with or different from each other, and denotes numbers which make the n value in the resulting compound of formula (2) 6 to 90, (ii) the compound of formula (4) is reacted with hydrohalic acid under a condition of pH 7 to 8 to produce an oil-miscible compound represented by the following formula (5):

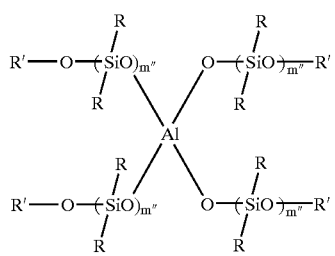

(5)

in which

R and R' are defined as previously described, and m'' is identical with or different from each other, and denotes numbers which make the n value in the resulting compound of formula (2) 6 to 90, and (iii) the compound of formula (5) is heated at temperatures ranging from 80 to 220° C.

During the procedure of preparing the compound of formula (2) via compounds 4 and 5, the number of siloxyl units(i.e., m' or m'') is increased due to the successive condensation reactions and the degree of increase may be determined by the amount of aluminum compound introduced. That is, the small amount of aluminum compound leads to a lot of condensation reactions which make the number of siloxyl units and ultimately the n value increase and vice versa. Therefore, it is another object of the present invention to provide such a preparation process.

The above process for preparing the compound of formula (2) may be summarized as the following Reaction Scheme 3.

[Reaction Scheme 3]

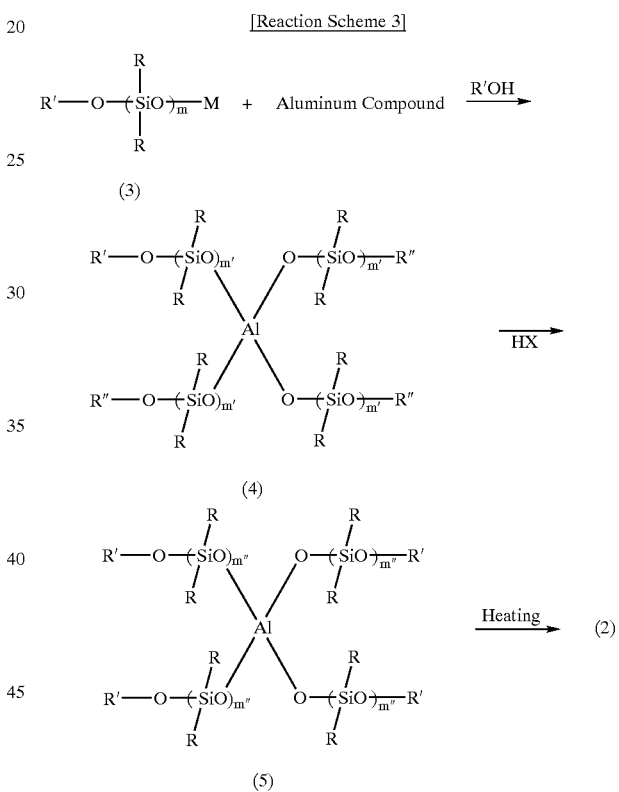

In Step (i) of the above process for preparing compound (2), the siloxane alkali metal salt of formula (3) includes any alkali metal salts, for example salts with lithium, sodium, potassium, etc., however sodium salt is preferable in view of the easiness of reaction and economy. As the reactant aluminum compound, aluminum metal, or hydroxide, oxide, alkali metal salt, halide, inorganic acid(sulfate, nitrate, etc.) salt of aluminum, such as for example, Al, $Al(OH)_3$, $Al_2O_3$, $AlCl_3$, $AlO_2Na$ may be used. Among them, aluminum metal is most preferable in view of the easiness of reaction and economy. Aluminum compound is used in an amount to make the Si/Al mole ratio in the resulting compound of formula (2) or (1) 12 to 180. As stated above, the n value of the final compound of formula (2) or (1) varies according to the amount of aluminum compound used. Reaction is carried out under room temperature or warming. Reaction temperature may be different according to the kind of aluminum compound used. For example, room temperature is preferred when aluminum metal is used, and some warming is required when aluminum chloride is used. Alcohol compound participated in the reaction should be secondary or tertiary alcohols, and isopropyl alcohol or t-butyl alcohol is particularly preferable. The resulting compound of formula (4) thus obtained by the reaction as explained above is hydrophilic.

In Step (ii), the compound of formula (4) is reacted with hydrohalic acid under a condition of pH 7 to 8 to produce the compound of formula (5). As the hydrohalic acid, hydrochloric acid, hydrobromic acid, hydroiodic acid, preferably hydrochloric acid can be used. The reaction is carried out by adding a basic compound to the reaction solution containing the compound of formula (4) first to make the solution alkaline (pH range of about 8 to about 10) and then by adding the reactant hydrohalic acid thereto in an amount required to control the pH value of the reaction solution to 7 to 8. As the basic compound, ammonia compound, particularly ammonia gas or ammonia water is used in an amount to make the reaction solution alkaline. When an alkali metal-containing compound is used as the basic compound instead of the ammonia compound, additional purification steps may be required depending on the purpose of the resulting aluminosiloxane compound and thus, not desirable. Through such a neutralization procedure, the oil-miscible and multi-functional compound of formula (5) is obtained.

Finally in Step (iii), the compound of formula (5) is heated under normal pressure and temperatures of 80 to 220° C., preferably 100 to 160° C. to produce the desired compound of formula (2) which does not have any terminal functional groups.

On the other hand, the aluminosiloxane compound of formula (1) according to the present invention, which is deficient in M, can be prepared by a process characterized in that (a) the compound of formula (2) is reacted with a compound represented by the followings formula (6)

NR'$_3$HX  (6)

in which
R' is defined as previously described, and
X represents halogen, in a non-polar solvent, or
(b) a compound represented by the following formula (7):

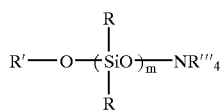  (7)

in which
R, R' and m are defined as previously described, and
R''' represents $C_1$–$C_6$-alkyl, is reacted with aluminum compound and secondary or tertiary alcohol, and then alcohol is removed therefrom.

In process variant (a) above, it is most preferable to use ammonium chloride(i.e., R' is hydrogen and X is chlorine) among the compound of formula (6) which is used as a reactant. Reaction is carried out for 3 to 5 hours under normal temperature and pressure because silicone oil may be separated from the resulting aluminosiloxane compound when the reaction mixture is heated. Since the compound of formula (6) is used for the purpose of removing M which is present in the compound of formula (2), it is preferable to use the compound of formula (6) in an equimolar amount to the compound of formula (2). As the non-polar solvent, one or more selected from n-hexane, toluene, tetrahydrofuran, bezene and xylene can be mentioned.

In process variant (b) above, if the compound of formula (7) is used as the starting material, the desired compound of formula (1) is directly produced without any need to use the hydrohalic acid. Here, the same aluminum compound and secondary or tertiary alcohol compound as explained in the process for preparing the compound of formula (2) may be used. When the compound of formula (7) is reacted with aluminum compound and alcohol, the reaction is preferably carried out at temperatures ranging from 60 to 80° C.

Although only aluminum compound is exemplified in the above processes according to the present invention, various forms of zinc(Zn) or tin(Sn) compound, such as for example, hydroxides, oxides, alkali metal salts, halides, acid addition salts(sulfate, nitrate, etc.) thereof besides the aluminum compound may be also reacted with siloxane alkali metal salt of formula (3) in the same manner as the aluminum compound to produce siloxane compounds containing various metals.

The present invention will be more specifically explained in the following examples. However, it should be understood that the following examples are intended to illustrate the present invention but not in any manner to limit the scope of the present invention.

BEST MODE FOR CARRYING OUT THE INVENTION

EXAMPLE 1

Step 1

100 ml of siloxane alkali metal salt of formula (3) (wherein R=methyl, R'=isopropyl, M=natrium, and m=3) which had been concentrated to have 50% siloxane content was introduced into a 1 l volumetric three-neck flask, 6 g of sodium aluminate(NaOAlO, Junsei Chemical Co. Lot No. 5K1180), 30 ml of distilled water and 50 ml of isopropyl alcohol were added thereto, and the whole reaction mixture was stirred vigorously for 3 hours at room temperature. Under stirring, the mixture was heated for 1 hour at 40° C. and for 1 hour at 60° C. Reaction was continued until the reaction mixture was changed to transparent liquid having a pale-brown colour. 30 ml of siloxane alkali metal salt of formula (3) which had been concentrated to have 50% siloxane content was further added and the resulting mixture was continuously stirred to room temperature to give a transparent liquid substance having a pale-brown colour (hydrophilic aluminosiloxane metal salt of formula (4)).

Step 2

To the transparent liquid substance prepared in Step 1 was added 20 ml of 28% ammonia water, which was then stirred for 2 hours at room temperature. Under continuous stirring, conc hydrochloric acid was slowly added dropwise to control the pH value of reaction solution to 7.5. Then, the reaction solution was stirred for 1 hour at 60° C. and cooled down to room temperature. 100 ml of n-hexane was added, and the resulting solution was stirred for 30 minutes and allowed to stand. Transparent supernatant was separated by a separatory funnel. The lower layer remained after taking the supernatant was extracted with n-hexane, the extract thus obtained was combined with the supernatant and washed with distilled water. The solvent was removed by a rotary evaporator to give oil- miscible aluminosiloxane compound (formula (5)).

Step 3

Figure 1:
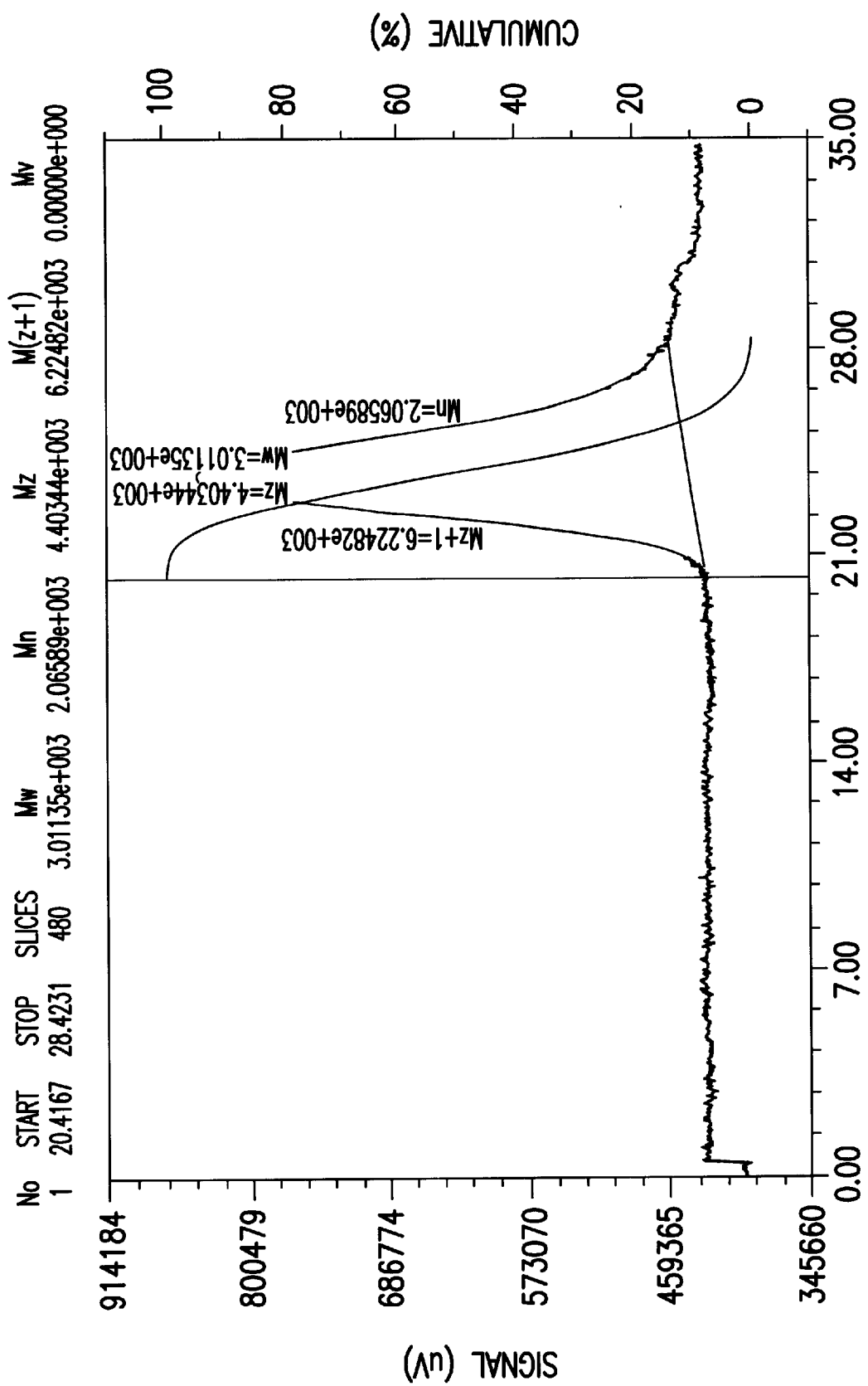
FIG. 1 shows G.P.C.(gel permeation chromatography) spectrum of aluminosiloxane compound of formula (2) prepared in Step 3 of Example 1(Al content 2.76%, Average molecular weight 2000, Mw/Mn=1.5)
Figure 2:
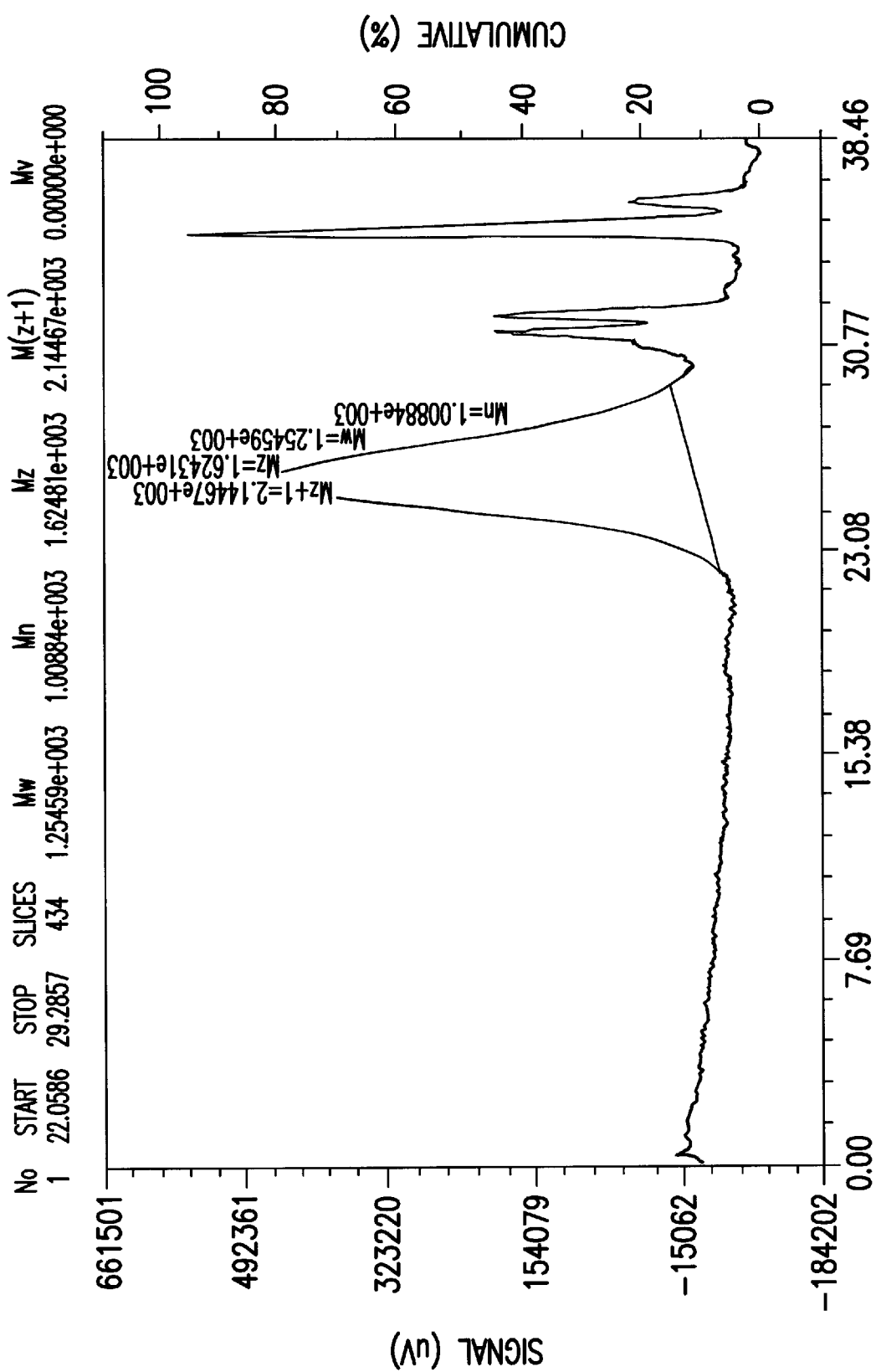
FIG. 2 shows G.P.C. spectrum of aluminosiloxane compound of formula (1) prepared by treating the aluminosiloxane compound of formula (2) in Step 3 of Example 1 with ammonium chloride and then by heating(Al content 2.85%; Average molecular weight 1000, Mw/Mn=1.25)
Figure 3:
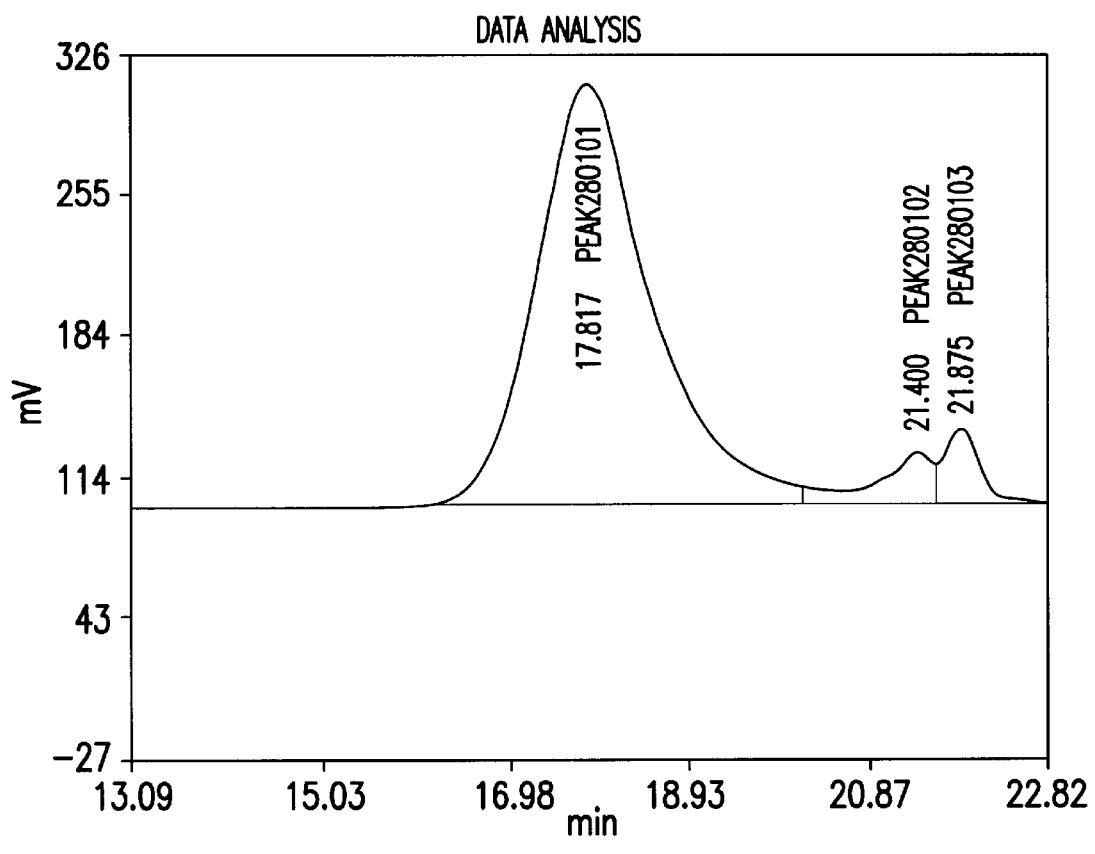
FIG. 3 shows G.P.C. spectrum of aluminosiloxane compound of formula (1) prepared in Example 5(Al content 0.52%; Average molecular weight 5462, Mw/Mn=1.46)
Figure 4:
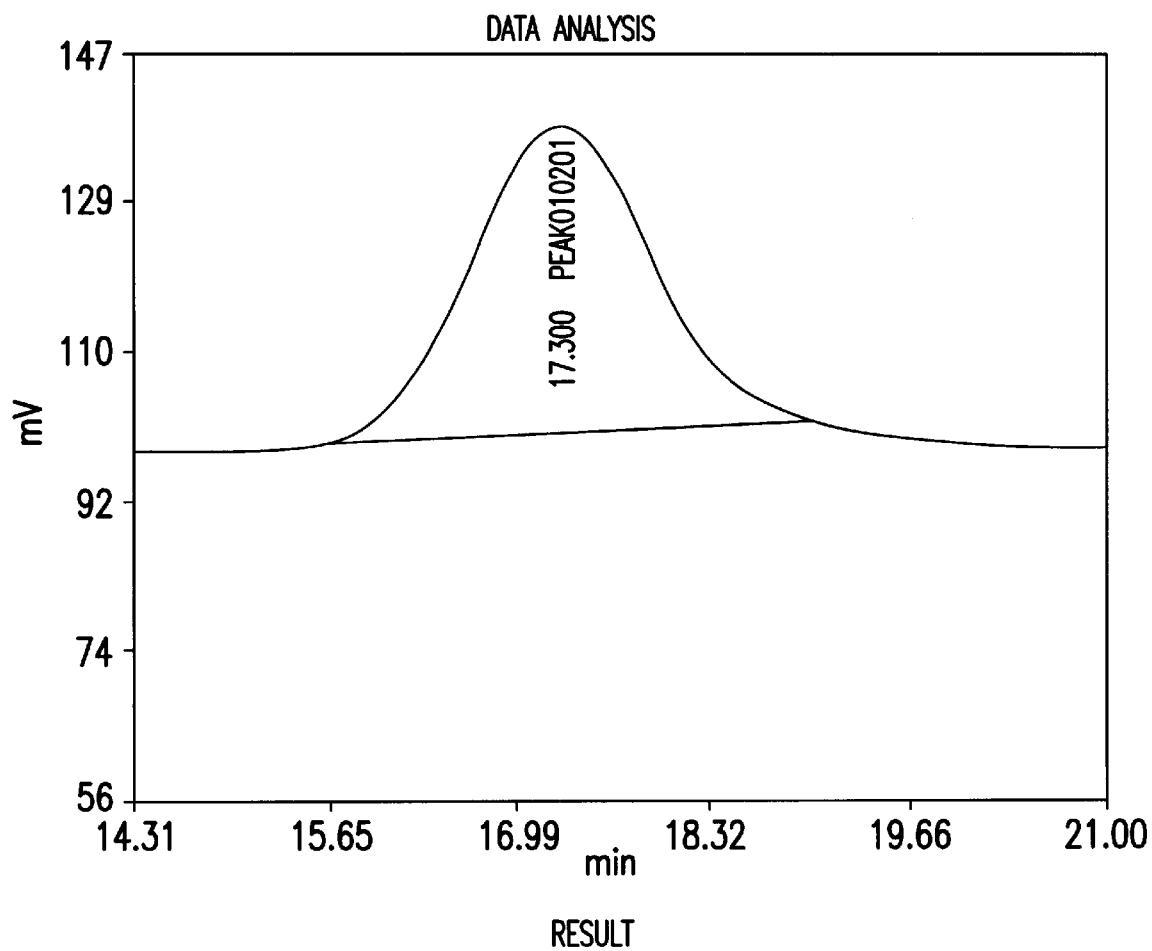
FIG. 4 shows G.P.C. spectrum of aluminosiloxane compound of formula (1) prepared in Example 6(Al content 0.3%; Average molecular weight 10948, Mw/Mn=1.32)
Figure 5:
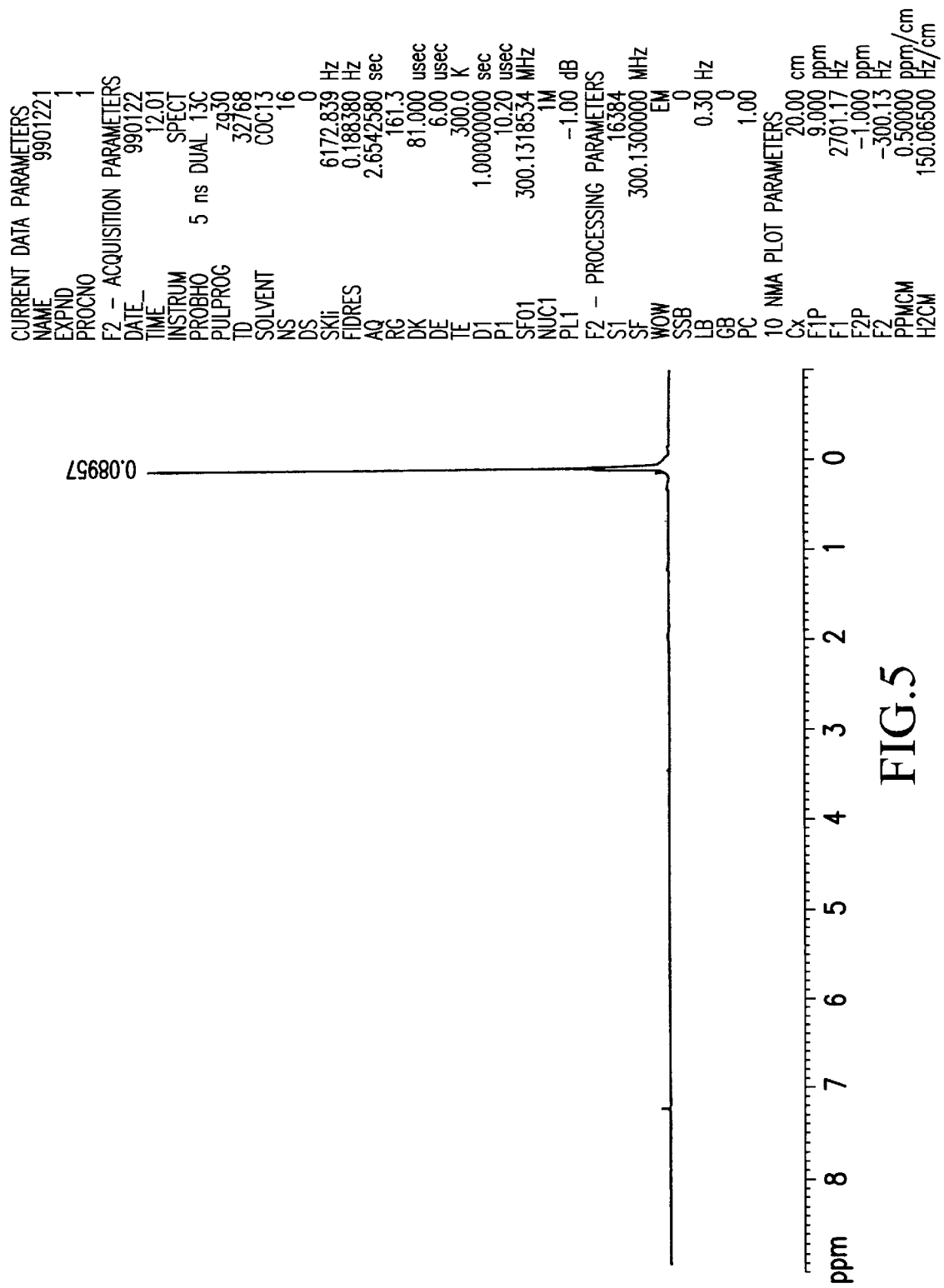
FIG. 5 shows $^1$H-NMR spectrum of aluminosiloxane compound of formula (1) prepared in Example 1(Average molecular weight 1000)
Figure 6:
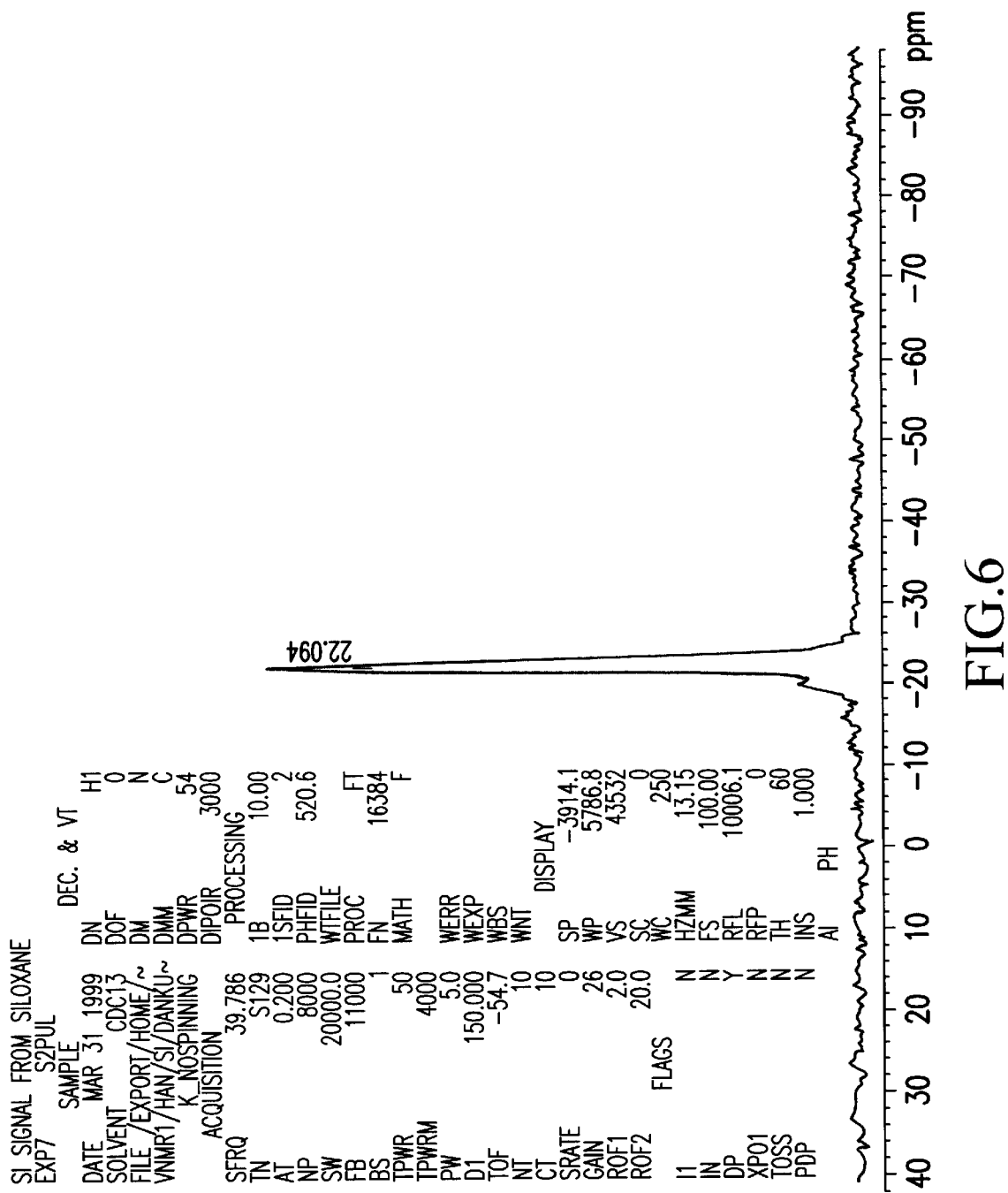
FIG. 6 shows $^{29}$Si-NMR spectrum of aluminosiloxane compound of formula (1) prepared in Example 1(Average molecular weight 1000)
Figure 7:
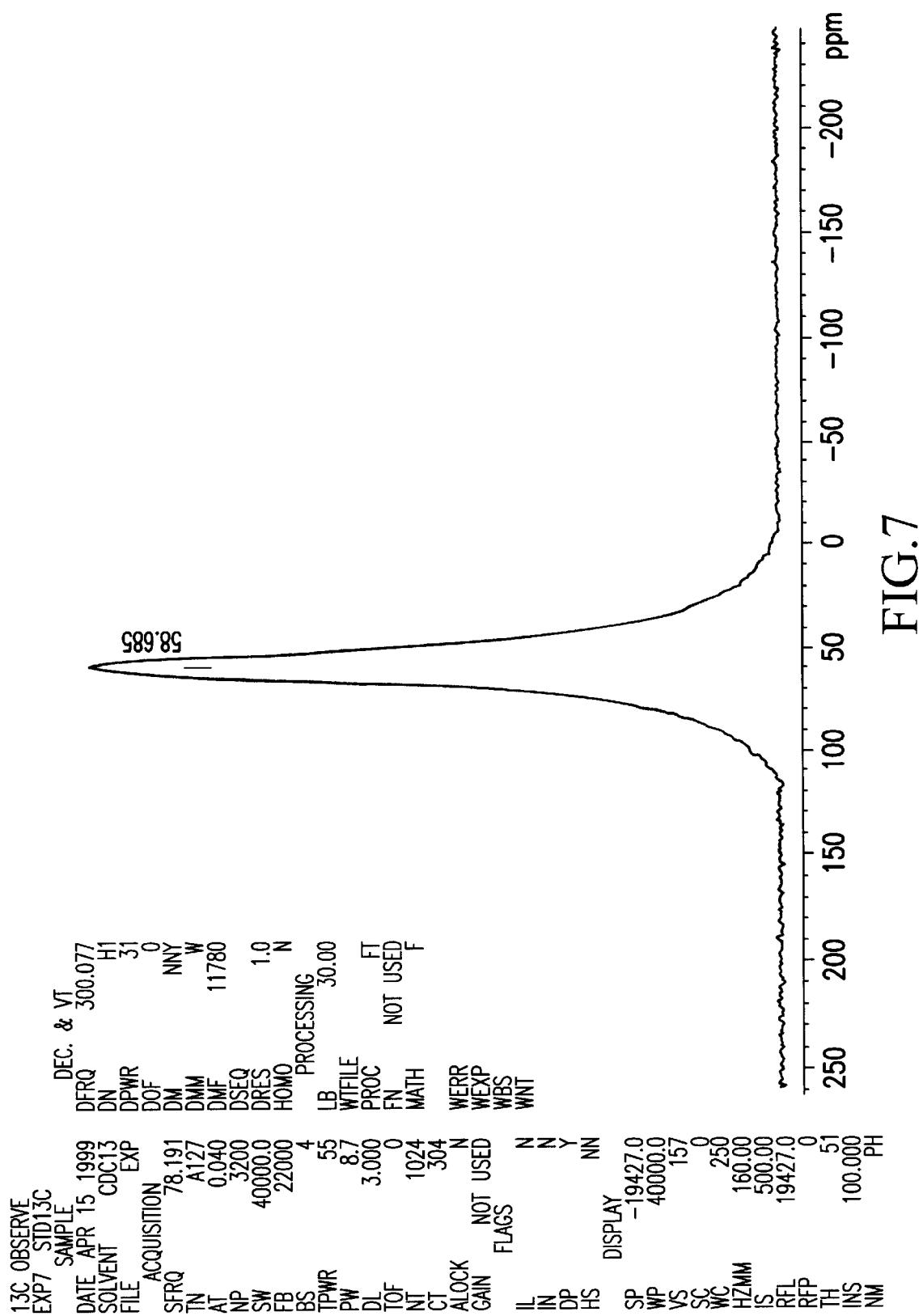
FIG. 7 shows $^{27}$Al-NMR spectrum of aluminosiloxane compound of formula (1) prepared in Example 1(Average molecular weight 1000).

The compound prepared in Step 2 was introduced into a 500 ml beaker, heated to 150° C. to be concentrated, and then cooled to give 60 g of aluminosiloxane compound (formula (2): R=methyl, M=natrium, n=6; Average molecular weight 2000) in the gel form of initial concentrate. The initial concentrate thus obtained was dissolved in 300 ml of n-hexane, 3 g(the same molar amount as that of alkali metal identified by elementary analysis) of ammonium chloride was added, and the mixture was stirred for 4 hours at room temperature. Supernatant was separated by a separatory funnel and the solvent therein was removed by heating the supernatant in a rotary evaporator of 150° C. to give 59 g of aluminosiloxane compound(formula (1): R=methyl, n=6; Average molecular weight 1000). This compound was dried in a vacuum oven of 30–40° C. for 24 hours to thoroughly remove the solvent, and thus dried compound was used as a sample for structural analysis. The sample was analyzed by $^{27}$Al-NMR and $^{29}$Si-NMR, and as a result, configurations of $AlO_4$ and $R_2SiO_2$ were identified(see FIGS. 6 and 7).

EXAMPLE 2

100 ml of siloxane salt used as a starting material in Example 1 was introduced into a 1 l volumetric three-neck flask, 8 g of aluminum hydroxide [Al(OH)$_3$, Aldrich cat. no. 23.918-6], 20 ml of distilled water and 50 ml of isopropyl alcohol were added thereto, and the whole reaction mixture was stirred well while being heated to 40–60° C. After the reaction mixture was changed to semitransparent liquid having a pale-brown colour, 30 ml of siloxane alkali metal salt of formula (3)(wherein R=methyl, R'=isopropyl, M=natrium, and m=3) was further added and the resulting mixture was continuously reacted under stirring at the same temperature to give a transparent liquid substance having a pale-brown colour. To the transparent liquid substance thus obtained was added 20 ml of 28% ammonia water. Conc. hydrochloric acid was slowly added dropwise thereto under stirring to control the pH value of reaction solution to 7.5. Then, the reaction solution was cooled down to room temperature, 100 ml of n-hexane was added, and the resulting solution was allowed to stand. Thereafter, the same procedure as Example 1 was carried out to give 61 g of aluminosiloxane compound(formula (2): R=methyl, M=natrium, n=6; Average molecular weight 2000) in the gel form of initial concentrate which was then treated with ammonium chloride to give 58 g of the desired aluminosiloxane compound(formula (1): R=methyl, n=6; Average molecular weight 1000).

EXAMPLE 3

The same procedure as Example 1 was carried out except that 5 g of aluminum oxide[Al$_2$O$_3$; Aldrich cat. no. 23.474-5; 100mesh] was used as the aluminum compound to give 58 g of aluminosiloxane compound(formula (2): R=methyl, M=natrium, n=6; Average molecular weight 2000) in the gel form of initial concentrate which was then converted to 56 g of aluminosiloxane compound (formula (1): R=methyl, n=6; Average molecular weight 1000).

EXAMPLE 4

The same procedure as Example 1 was carried out except that 2 g of powdered aluminum metal(Aldrich cat. no. 20.258-4) was used as the aluminum compound to give 61 g of aluminosiloxane compound(formula (2): R=methyl, M=natrium, n=6; Average molecular weight 2000) in the gel form of initial concentrate which was then converted to 60 g of aluminosiloxane compound (formula (1) R=methyl, n=6; Average molecular weight 1000).

EXAMPLE 5

The same procedure as Example 1 was carried out except that 0.4 g of powdered aluminum metal(Aldrich cat. no. 20.258-4) was used as the aluminum compound to give 59 g of aluminosiloxane compound(formula (1): R=methyl, n=35; Average molecular weight 5,462) in the form of gel semisolid.

EXAMPLE 6

The same procedure as Example 1 was carried out except that 0.2 g of powdered aluminum metal(Aldrich cat. no. 20.258-4) was used as the aluminum compound to give 60 g of aluminosiloxane compound(formula (1): R=methyl, n=65; Average molecular weight 10,948) in the form of gel semisolid(softer than the product of Example 5).

EXAMPLE 7

100 g of methylphenylsilicone oil(purchased from Shinetsu Co., Japan; Kf54) was introduced into a 500 ml polyethylene vessel, 100 ml of methanol, 100 ml of isopropyl alcohol and 12 g of NaOH were added thereto, and the resulting mixture was reacted for 24 hours at room temperature under shaking to completely decompose the silicone oil and simultaneously to prepare siloxane alkali metal salt of formula (3)(wherein R=methyl or phenyl, R'=isopropyl, M=natrium, and m=3). Thereafter, the same procedure as Example 1 was carried out except that 1.5 g of powdered aluminum metal (Aldrich cat. no. 20.258-4) was used as the aluminum compound to give 62 g of aluminosiloxane compound(formula (1): R=methyl or phenyl, n≈7.5; Average molecular weight 1,462) in the form of gel semisolid.

EXAMPLE 8

100 g octamethylcyclotetrasiloxane(Aldrich cat. no. 23.569-5) was introduced into a 1 l polyethylene vessel, 100 ml of isopropyl alcohol was added together with 100 ml of tetramethylammoniumhydroxide(Aldrich cat. no. 33.490-1, 25% in methanol) thereto, and the vessel was sealed. The resulting mixture was reacted for 24 hours at room temperature under shaking to completely decompose the silicone oil and simultaneously to prepare siloxane salt of formula (7)(wherein R=methyl, R'=isopropyl, R'''=methyl, and m=3). The reactants were introduced into a 1 l volumetric three-neck flask, 1.8 g of powdered aluminum metal(Aldrich cat. no. 20.258-4) was weighed out and added, and then the resulting mixture was stirred well for 6 hours at room temperature and 20 hours at 60~80° C. under reflux-heating. After identifying that powdered aluminum metal was dissolved in a transparent state, the mixture was cooled down to room temperature. 300 ml of n-hexane and 100 ml of distilled water were added and the supernatant was separated by a separatory funnel. This supernatant was concentrated in a 500 ml beaker by evaporating the solvent. The concentrate was allowed to stand in a vacuum oven(40 torr, 50° C.) for 48 hours to remove the remaining solvent and finally to give 94 g (Yield 90%) of aluminosiloxane compound(formula (1): R=methyl, n≈6; Average molecular weight 1,120) in the form of gel semisolid.

EXAMPLE 9

100 ml of siloxane alkali metal salt of formula (3) (wherein R=methyl, R'=isopropyl, M=natrium, and m=3) used as a starting material in Example 1 was introduced into a 1 l volumetric three-neck, flask and 100 ml of isopropyl alcohol and 100 ml of n-hexane were added thereto. After the flask was equipped Wraith a reflux condensor, 12 g of aluminum chloride[AlCl$_3$—6H$_2$O, Aldrich cat. no. 23.707-8] was added under vigorous stirring, and the resulting mixture was reacted under heating at 60° C. This reaction was carried out with bubbles, and thus, the reaction was controlled by lowering the temperature if the bubbling is too vigorous and by further adding aluminum chloride if the pH value of the reaction solution did not reach 7.5. The reaction mixture was stirred for 1 hour at the same temperature under heating and then allowed to stand. Transparent supernatant was separated and then washed three times with distilled water. Thereafter, the same procedure as Example 1 was carried out to give 55 g of aluminosiloxane compound (formula (2): R=methyl, M=natrium, n=6; Average molecular weight 2000) in the gel form of initial concentrate which was then converted to 53 g of the aluminosiloxane compound (formula (1): R=methyl, n=6; Average molecular weight 1000).

EXAMPLE 10

Siloxylation of Cellulose 100 g of the compound of formula (1) having an average molecular weight of 1000(prepared in Example 1) was dissolved in 500 ml of n-hexane. 10 g of cellulose fabric was soaked in 100 ml of said solution. The fabric was dried under atmosphere, soaked in 0.5 ml of formic acid and then dried. The dried fabric was heated at 130–150° C. to siloxylate hydroxy groups on the surface of the cellulose. It was identified by a contact analyzer that the cellulose thus siloxylated has the water repellence which leads to a contact angle of water drop of 100–110°.

EXAMPLE 11

Siloxylation of Novorak Phenol Resin 10 g of Novorak phenyl resin(Molecular weight 600–1500) was dissolved in 50 ml of n-butanol, sawdust finely pulverized was added thereto in a ratio of 1:1 by weight with respect to the phenol resin and then mixed well. The mixture was treated with warm wind of 50° C. to remove the solvent and the resulting residue was finely pulverized. To the pulverized residue was introduced a solution wherein 2 g of the compound of formula (1) having an average molecular weight of 1000(prepared in Example 1) was dissolved in 10 ml of n-hexane. The mixture was mixed well and allowed to stand for 24 hours at room temperature to be matured. The mature mixture was introduced into a mold, heated to about 150° C., condensed, and hardened under degassing. The siloxylated phenol resin thus obtained exhibits improved physico-chemical properties such that no silicone oil is separated from the resin surface, there is no need to use an agent for mold release during the processing, and gloss and flexibility are improved.

EXAMPLE 12

Siloxylation of Epoxy Resin 10 g of the compound of formula (1) having an average molecular weight of 1000(prepared in Example 1) was dissolved in 30 ml of xylene. 2 g of epoxy resin(YD-011 of Kukdo Chemical Co., Ltd.), which has a molecular weight of about 800 to 1000 and is prepared from bisphenol A and epichlorohydrin, was added to said aluminosiloxane-xylene solution and dissolved under stirring. The resulting solution was heated for 20 minutes at 140–150° C. The reaction solution was continuously stirred and cooled down to room temperature. 10 ml of xylene and 15 g of epoxy resin(YD-011) were sequentially added thereto, which were dissolved and mixed together under vigorous stirring at 60–80° C. The mixture was cooled down to room temperature and G-1034 (Kukdo Chemical Co., Ltd.) was added thereto as a hardening agent in an amount of ¼ part by weight with respect to the epoxy resin. Surface of flat glass was coated with the resulting product in a thickness of 0.3–0.4 mm and the coating layer was hardened for 4 days at room temperature. By observing the surface, it was identified that 1) adhesion force of the coating layer with the surface of glass is significantly increased, 2) no silicone oil is separated from the surface, 3) the surface is more elastic than that coated with epoxy resin which is not siloxylated, and 4) the surface gloss is excellent.

INDUSTRIAL APPLICATION

According to the present invention, waste silicone compounds may be recycled, particularly reused as expensive products. That is, waste compounds containing siloxane bonds may be converted to the aluminosiloxane compound of formula (1) or (2), which can be used as a highly effective siloxylating agent.

What is claimed is:

1. An aluminosiloxane compound represented by the following formula (1):

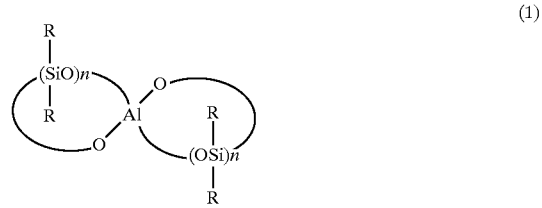

(1)

in which

R is identical with or different from each other, and represents C$_1$–C$_6$-alkyl or phenyl, and n denotes a number of 6 to 90.

2. An aluminosiloxane compound represented by the following formula (2):

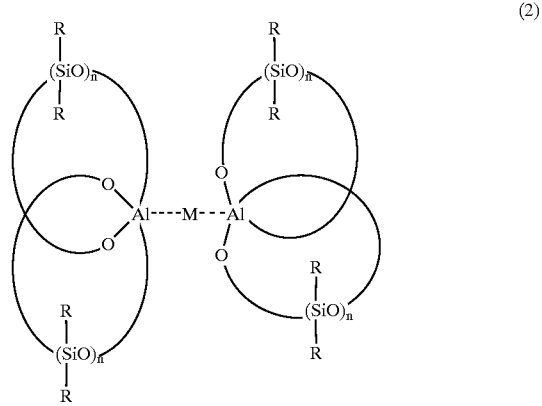

(2)

in which

R is identical with or different from each other, and represents $C_1$–$C_6$-alkyl or phenyl, n denotes a number of 6 to 90, and M represents alkali metal.

3. A process for preparing the aluminosiloxane compound of formula (2) as defined in claim 2 characterized in that (i) the siloxane alkali metal salt represented by the following formula (3):

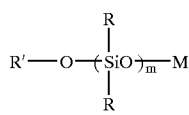
(3)

R is identical with or different from each other, and represents $C_1$–$C_6$-alkyl or phenyl, R' is identical with or different from each other, and represents hydrogen or $C_1$–$C_6$-alkyl, M represents alkali metal, and m denotes a number of 3 to 6, is reacted with aluminum compound and secondary or tertiary alcohol to produce a hydrophilic compound represented by the following formula (4):

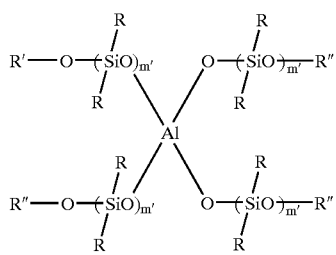
(4)

in which

R and R' are defined as previously described,

R" is identical with or different from each other, and represents R' or M, but with at least one of R" being different from R', and m' is identical with or different from each other, and denotes numbers which make the n value in the resulting compound of formula (2) 6 to 90, (ii) the compound of formula (4) is reacted with hydrohalic acid under a condition of pH 7 to 8 to produce an oil-miscible compound represented by the following formula (5):

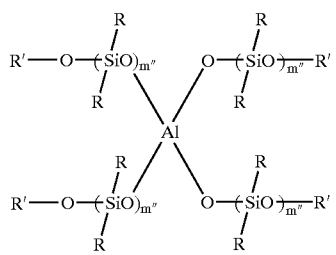
(5)

in which

R and R' are defined as previously described, and m" is identical with or different from each other, and denotes numbers which make the n value in the resulting compound of formula (2) 6 to 90, and (iii) the compound of formula (5) is heated at temperatures ranging from 80 to 220° C.

4. The process of claim 3, wherein the n value in the compound of formula (2) finally produced is adjusted by controlling the amount of aluminum compound used in Step (i).

5. The process of claim 3, wherein the aluminum compound is used in an amount to make the Si/Al mole ratio in the compound of formula (2) 12 to 180 in Step (i).

6. The process of claim 3, wherein one selected from a group consisting of aluminum metal, hydroxide, oxide, alkali metal salt, halide and inorganic acid salt of aluminum is used as the aluminum compound in Step (i).

7. The process of claim 3, wherein the reaction of Step (ii) is carried out by adding a basic compound to the reaction solution containing the compound of formula (4) to make the solution alkaline and then by adding hydrohalic acid thereto in an amount required to control the pH value of the reaction solution to 7 to 8.

8. The process of claim 7, wherein the basic compound is ammonia gas or ammonia water.

9. The process of claim 7, wherein hydrohalic acid is one or more selected from a group consisting of hydrochloric acid, hydrobromic acid and hydroiodic acid.

10. A process for preparing the aluminosiloxane compound of formula (1) as defined in claim 1 characterized in that (a) the compound of formula (2) as defined in claim 2 is reacted with a compound represented by the following formula (6):

$NR'_3HX$ (6)

in which

R' is defined as claim 3, and

X represents halogen, in a non-polar solvent, or (b) a compound represented by the following formula (7):

(7)

in which

R, R' and m are defined as claim 3, and

R'" represents $C_1$–$C_6$-alkyl, is reacted with aluminum compound and secondary or tertiary alcohol, and then alcohol is removed therefrom.

11. The process of claim 10, wherein the compound of formula (6) is used in an equimolar amount to the compound of formula (2).

12. The process of claim 10, wherein the reaction of process variant (b) is carried out at temperatures ranging from 60 to 80° C.

13. A siloxylating agent comprising the compound defined in claim 1.

14. The process of claim 4, wherein the aluminum compound is used in an amount to make the Si/Al mole ration in the compound of formula (2) 12 to 180 in Step (i).

15. The process of claim 4, wherein one selected from a group consisting of aluminum metal, hydroxide, oxide, alkali, metal salt, halide and inorganic acid salt of aluminum is used as the aluminum compound in Step (i).

16. A siloxylating agent comprising the compound defined in claim 2.

* * * * *